United States Patent [19]

Lam et al.

[11] Patent Number: 5,496,547

[45] Date of Patent: Mar. 5, 1996

US005496547A

[54] PSEUDOMONAS BIOCONTROL STRAINS

[75] Inventors: Stephen Lam, Raleigh; Nancy Torkewitz, Hurdle Mills, both of N.C.

[73] Assignee: Ciba-Geigy Corporation, Tarrytown, N.Y.

[21] Appl. No.: 185,623

[22] Filed: Jan. 24, 1994

[51] Int. Cl.$^6$ .............................. A01N 63/00; C12N 1/20; C12N 15/00; C12N 1/21

[52] U.S. Cl. ........................... 424/93.47; 435/172.1; 435/876; 435/253.3; 435/252.34; 504/117; 47/58; 47/57.6

[58] Field of Search .................. 424/93.47; 435/252.34, 435/876, 243, 172.1, 253.3; 504/117; 935/10; 47/57.6, 58

[56] References Cited

U.S. PATENT DOCUMENTS

4,647,537  3/1987  Shigemitsu .......................... 435/178

FOREIGN PATENT DOCUMENTS

0472494A2  12/1991  European Pat. Off. ..
0472495A2  2/1992  European Pat. Off. ........ C12N 15/52

OTHER PUBLICATIONS

Baker et al., "Examples of Biological Control", *Biological Control of Plant Pathogens*, 61–106 (1982).
Howell et al., "Control of *Rhizoctonia solani* on Cotton Seedlings with *Pseudomonas fluorescens* and With an Antibiotic Produced by the Bacterium", *Phytopathology*, 69(5): 480–482 (1979).
Kloepper et al., "Relationship of in vitro Antibiosis of Plant Growth–Promoting Rhizobacteria to Plant Growth and the Displacement of Root Microflora", *Phytopathology*, 71 (10): 1020–1024 (1981).
Kraus et al., "TN5 Insertion Mutants of *Pseudomonas fluorescens* Pf–5 Altered in Production of the Antibiotics Pyrrolnitrin and Pyoluteorin", Abstract, *The American Phytopathological Society*, Pacific Division Jun. 20–21, 1989.
Pfender et al., "A Genomic Region from *Pseudomonas fluorescens* Pf–5 Required for Pyrrolnitrin Production and Inhibition of *Pyrenophora tritici–repentis* in Wheat Straw", *The American Phytopathological Society*, 83 (11): 1223–1228 (1993).
Salcher et al., "Isolation and Characterization of a Mutant of *Pseudomonas aureofaciens* ATCC 15926 with an Increased Capacity for Synthesis of Pyrrolnitrin", *Journal of General Microbiology*, 118: 509–513 (1980).
Scher et al., "Mechanism of Biological Control in a Fusarium–Suppressive Soil", *Phytopathology*, 70: 412–417 (1980).
Weller et al., "Suppression of Take–All of Wheat by Seed Treatments with Fluorescent Pseudomonads", *Phytopathology*, 73 (3): 463–469 (1983).

*Primary Examiner*—David T. Fox
*Assistant Examiner*—Elizabeth F. McElwain
*Attorney, Agent, or Firm*—Andrea C. Walsh

[57] ABSTRACT

Mutant strains of Pseudomonas have been isolated which have enhanced biocontrol properties. The strains are particularly useful against *Rhizoctonia solani*.

5 Claims, No Drawings

PSEUDOMONAS BIOCONTROL STRAINS

FIELD OF THE INVENTION

The present invention relates to the identification of mutant strains of Pseudomonas which have improved biocontrol properties, More specifically it relates to strains which are effective against plant pathogenic fungi.

BACKGROUND OF THE INVENTION

It has been recognized that crops grown in some soils are naturally resistant to certain fungal pathogens. Furthermore, soils that are conducive to the development of these diseases can be rendered suppressive or resistant to the pathogen by the addition of small quantities of soil from a suppressive field (Scher and Baker (1980) Phytopathology 70: 412–417). Conversely, suppressive soils can be made conducive to fungal disease susceptibility by autoclaving, indicating that the factors responsible for disease control are biological. Subsequent research has demonstrated that root colonizing bacteria are responsible for this phenomenon which is known as biological disease control (Cook and Baker (1983), The Nature and Practice of Biological Control of Plant Pathogens; Amer. Phytopathol. Soc., St Paul, Minn.).

In many cases, the most efficient strains of biological disease controlling bacteria are fluorescent pseudomonads (Weller et al. (1983) Phytopathology, 73: 463–469). These bacteria have also been shown to promote plant growth in the absence of a specific fungal pathogen by the suppression of detrimental rhizosphere microflora present in most soils (Kloepper et al. (1981) Phytopathology 71: 1020–1024). Important plant pathogens that have been effectively controlled by seed inoculation with these bacteria include *Gaemannomyces graminis*, the causative agent of take-all in wheat (Cook et al. (1976) Soil Biol. Biochem 8: 269–273) and Pythium and Rhizoctonia, pathogens which cause damping off of cotton (Howell et al. (1979)Phytopathology 69: 480–482). Rhizoctonia is a particularly problematic plant pathogen for several reasons. Firstly, it is capable of infecting a wide range of crop plants and secondly, there are no commercially available chemical fungicides that are effective in controlling the fungus.

Many biological disease controlling Pseudomonas strains produce antibiotics that inhibit the growth of fungal pathogens (Howell et al. (1979) Phytopathology 69: 480–482; Howell et al. (1980) Phytopathology 70: 712–715). These antibiotics have been implicated in the control of fungal pathogens in the rhizosphere. In particular, Howell et al. (Phytopathology 69: 480–482; 1979) disclose a strain of *Pseudomonas fluorescens* which was shown to produce an antibiotic substance that is antagonistic to *Rhizoctonia solani*. Indeed, several past studies have focused on the effects of mutations that result in the inability of the disease control bacterium to synthesize these antibiotics (Kloepper et al. (1981) Phytopathology 71: 1020–1024; Howell et al. (1983) Can. J. Microbiol. 29: 321–324). In these cases, the ability of the organism to control the pathogen is reduced, but not eliminated.

An important factor in biological control is the ability of an organism to compete in a given environment (Baker et al. (1982) Biological Control of Plant Pathogens, American Phytopathological Society, St. Paul, Minn., pages 61–106). Thus, it is desirable to obtain strains of biocontrol agents which are effective to control the growth of *Rhizoctonia solani* and other fungi and also able to aggressively compete with indigenous bacteria and microflora that exist in the rhizosphere of the plant.

SUMMARY OF THE INVENTION

The present invention is drawn to biocontrol strains of bacteria that are able to effectively control pathogenic attack on crop plants. The biocontrol strains of the invention produce at least one antifungal substance capable of inhibiting a broad spectrum of plant pathogens. Such strains have increased biocontrol properties and are able to aggressively compete in the plant rhizosphere. Methods of making the biocontrol strains as well as methods of using the strains for control of pathogenic attack on crops are described.

DETAILED DESCRIPTION OF THE INVENTION

The present invention provides improved biocontrol strains which can be used to control pathogenic attack on crop plants. Such strains are able to aggressively compete in the plant rhizosphere as well as produce one or more antifungal substances that are effective against a broad spectrum of plant pathogenic fungi, particularly Rhizoctonia, more particularly *Rhizoctonia solani*.

The biocontrol strains of the present invention are important for several reasons. Firstly, *Rhizoctonia solani* is a particularly pernicious plant pathogen. The affected plants include beans, wheat, tomato and potato, in addition to cotton. Secondly, there are no environmentally safe and effective fungicide treatments available for the protection of crops from *Rhizoctonia solani*. Therefore, the use of the disclosed biocontrol strains to control or prevent *Rhizoctonia solani* infections in crop plants provide the first environmentally safe and effective method of control of this pathogen.

The biocontrol strains of the present invention are made by preparing a collection of insertion mutants as described in the Experimental section below. Such insertion mutant strains are then screened for in vitro fungal inhibition activity. Those strains which demonstrate the desired activity are then further characterized in greenhouse and field biocontrol assays.

In one embodiment of the invention, using molecular biological techniques, the plasmid pCIB116 was constructed. pCIB116 is suitable for use in transposon mutagenesis and was transferred to Pseudoraonas strain CGA 267356 (a.k.a. 11c-1-38—see EP 0 472 494 A2; ATCC #55169) to generate a collection of insertion mutants. Suitable methods for transfer of pCIB116 and other such plasmids to Pseudomonas CGA 267356 are known in the art. Simon et al. (1983) Bio/Technology 1: 784–791. Preferred methods for the transfer of DNA to Pseudomonas include conjugation from *E. coli* and electroporation. Maniatis et al., (1989) Molecular Cloning, Ch. 1, Cold Spring Harbor Laboratory Press, New York.

In addition, the nature of the plasmid is not critical to the invention; it is sufficient that part of the transferred plasmid is able to transpose to various loci within the Pseudomonas genome and form a library of insertion transposon mutants which can subsequently be screened. Thus a library of approximately 10000 different insertion mutants of Pseudomonas were generated. These were tested for their ability to inhibit growth of the fungus Neurospora in vitro. Mutants were isolated which produced antifungal clearing zones which were distinctive from wild-type and these were tested for their ability to control infestation by the fungus

*Rhizoctonia solani* of cotton in glasshouse tests. Two insertion mutants were found to provided better disease control against Rhizoctonia in tests on cotton. These two Pseudomonas strains (CGA 319115 and CGA 321730) had enhanced properties as biocontrol strains when compared to the parent strain CGA 267356. These two Pseudomonas strains have been deposited in connection with this application under 37 C.F.R. § 1.802 on Jan. 21, 1994 with the Agricultural Research Service Culture Collection (NRRL), an International Deposit Authority recognized under the Budapest Treaty and given the accession numbers NRRL B-21172 and NRRL B-21173, respectively.

It is recognized that strains can be isolated which display the capacity to control a single or a range of fungal plant pathogens. Thus, in one embodiment of the invention strains are provided which have enhanced biocontrol properties against the fungus *Rhizoctonia solani*. In a further embodiment of the invention strains are provided which have enhanced biocontrol properties against a range of fungal plant pathogens.

A further embodiment of the invention provides a method for controlling or inhibiting the growth of a plant pathogenic fungus by applying the biocontrol strains of the instant invention to an environment in which the plant pathogenic fungus may grow. This could be to the plant/s or parts of the plant/s or seeds (prior to planting) of the plant/s to be protected, or alternatively to soil in which the plant/s to be protected are growing or will grow. The strains will be applied in an effective amount. That is, in an amount sufficient to control or inhibit the pathogen. The rate of application may vary according to the crop to be protected, the efficacy of the biocontrol strain, the pathogen to be controlled, and the severity of the disease pressure. Generally, the rate of application will be about $1.3 \times 10^5$ cfu/cm to about $1.3 \times 10^{10}$ cfu/cm, specifically about $1.3 \times 10^6$ cfu/cm to about $1.3 \times 10^9$ cfu/cm, more specifically about $1.3 \times 10^7$ cfu/cm to about $1.3 \times 10^8$ cfu/cm.

Another embodiment of the present invention provides methods of inhibiting the growth of the fungus *Rhizoctonia solani* by applying the biocontrol strains of the instant invention to an environment in which the plant pathogenic fungus may grow. This could be to the plant/s or parts of the plant/s or seeds (prior to planting) of the plant/s to be protected, or alternatively to soil in which the plant/s to be protected are growing or will grow. As noted above, the rate of application will vary depending on various factors. However, the general rate of application will be about $1.3 \times 10^5$ cfu/cm to about $5 \times 10^9$ cfu/cm, specifically about $1.3 \times 10^6$ cfu/cm to about $1.3 \times 10^9$ cfu/cm more specifically about $1.3 \times 10^7$ cfu/cm to about $1.3 \times 10^8$ cfu/cm.

A further embodiment of the present invention provides a method for the isolation of novel biocontrol strains comprising the steps of (1) creating a library of transposon insertion mutants in a Pseudomonas strain; (2) testing said mutants for their ability to inhibit the growth of a test fungus such as Neurospora in vitro; (3) comparing the zones of clearing in the test fungus produced by wild-type non-mutant and mutant strains; (3) selecting mutants which produce zones of clearing which are distinctive from the zones of clearing of the wild-type non mutant strain; and (4) further selecting these isolated mutants for their biocontrol properties on plant pathogenic fungi using biocontrol tests which are well known in the art.

The recombinant biocontrol agents of the present invention may be used in any manner known in the art, including coating seeds with an effective amount of the biocontrol agent, or in furrow application of the biocontrol agent directly into the soil and foliar application. Such methods are well known in the an and are described, for example, in the published European Application EP 0 472 494 A2. Furthermore, the strains of this application can also be mixed in formulation with known pesticides in a manner described in co-pending application 07/977,318, which disclosure is herein incorporated by reference.

The following Examples are offered by way of illustration and not by way of limitation.

EXPERIMENTAL

EXAMPLE 1

Construction of pCIBI100

The plasmid pLRKΔ211 (Kroos and Kaiser, PNAS 81: 5816–5820; 1984) contains a Tn5-lac transposable element (encoding resistance to kanamycin) with a promoterless (in *E. coli*) trp-lac gene fusion inserted in IS50L of Tn5 in the correct orientation to fuse lacZ expression to promoters outside of Tn5. A new plasmid, pCIB100, was constructed by introducing the mobilization (mob) site from the plasmid pSUP5011 (Simon et al., In: Molecular Genetics of Bacteria-Plant Interaction; Puhler, A (Ed) pp 98–106; Springer Verlag, 1983) into pLRKΔ211, thus enabling the plasmid to be transferred to pseudomonads or other gram negative bacteria by conjugation. The plasmids pSUP5011 and pLRKΔ211 were digested individually with SalI and HindIII, and the resulting fragments were separated by electrophoresis in low melting point agarose. The DNA band corresponding to the SalI-HindIII fragment which contains the trp-lac fusion in pLRKΔ211 was cut from the gel and added to a similarly obtained SalI-HindIII fragment which contains the mob site from pSUP5011. Ligation was carried out in agarose (Methods of Enzymology; Vol. 101, Ch 3; Academic Press. New York).

The trp-lac fusion reporter gene in pCIB100 was found to confer constitutive lacZ gene expression in Pseudomonas. Applicants made a lac construct without the trp region and showed that it behaved satisfactorily as a promoterless reporter gene. A plasmid containing this construct was designated pCIB116.

EXAMPLE 2

Construction of pCIB114

The plasmid pMC874 (Casadaban et al., J Bacteriol. 143: 971–980; 1980) carries a portion of the lac operon which lacks the coding region for the first 8 amino acids of lacZ (a promoterless, incomplete gene designated lacZ'). This plasmid is useful in constructing a precursor plasmid of a subsequent plasmid that may be used according to the method of the invention to prepare insertion mutants. In this embodiment of the invention, plasmid pMC874 was digested with SalI and a synthetic oligonucleotide pair of the following structure was ligated to the SalI ends:

5'-TCGAGATCTAAA-3' (seq. ID No. 1)

3'-CTAGATTT-5' (seq. ID No. 2)

The resulting mixture was digested with BglII and ligated with BglII digested pRK290 (Ditta et al., PNAS 77: 7347–7351; 1980). This construct was designated pCIB113.

A synthetic oligonucleotide pair of the following sequence was constructed:

5'-AAAGGAGATCTGGATCCAGGAGAAGCTTGCATGCTA-3' (seq. ID No. 3)

3'-TTTCCTCTAGACCTAGGTCCTCTTC-GAACGTACGCTTAG-5' (seq. ID No. 4)

This oligonucleotide pair, when fused to the 5' end of the promoterless lacZ' gene, would supply the following sites (in order): BglII-BamHI-*E.coli* ribosome binding site-HindIII-SphI(ATG for translation start)-BglII end.

Plasmid pCIB113 was digested with BamHI, and was ligated to the synthetic oligonucleotide pair described above. The structure of the oligonucleotide pair forces ligation in a single orientation, with the BglII end ligated to the BamHI end of lacZ' and resulting in loss of the BamHI site. The construct was then digested with BglII, and the small (3.0 kb) oligo+lacZ'+lacY fragment was isolated and purified from agarose. To make plasmid pCIB114, a fragment isolated and purified in this manner was ligated to BglII-digested pRK290.

EXAMPLE 3

Construction of pCIB116

(1) The plasmid pCIB100 was digested with BamHI and HindIII. The large fragment carrying IS50L (the leftmost 54 base pairs), the colE1 origin of replication, and the left half of IS50R, was isolated and purified from agarose.

(2) The plasmid pCIB100 was digested with EcoR1 and HindIII. The large fragment carrying IS50R (right half), the mob gene, the Kan marker, and the promoter-distal portion of the lacZ-lacY fragment, was isolated and purified from agarose.

(3) The plasmid pCIB114 was digested with BamHI and EcoR1. The fragment carrying the lacZ portion of the molecule was isolated and purified from agarose gels. It was then mixed with the fragments isolated in steps (2) and (3) above. The mixture was ligated and used to transform *E. coli* HB101. Kanamycin resistant colonies were selected, and plasmid DNA was isolated from the transformants and analyzed for the correct orientation of fragments. The SalI site was removed by digestion with SalI, filling in the ends with Klenow fragment and blunt end ligation. Maniatis et al., (1989) Molecular Cloning, Ch. 1, Cold Spring Harbor Laboratory Press, New York. The sequence of the region of the plasmid containing the oligonucleotide junction with IS50L was confirmed using the dideoxy chain termination procedure. The final construct was designated pCIB116.

EXAMPLE 4

Construction of an Insertion Mutant Collection of Strain CGA 267356 (i.e. strain 11c-1-38) using pCIB116

The plasmid pCIB116 was transromped into *E. coli* strain S17-1 (R. Simon et al., 1983) using standard procedures (Maniatis et al. 1989). The resulting strain (S17-1/pCIB116) was used as donor for the introduction of pCIB116 into the Pseudomonas strain CGA267256 by conjugation. The *E. coli* (S17-1/pCIB116) and Pseudomonas strains were grown overnight at 37° C. in LB. 0.1 ml of each strain was mixed and spread onto LB plates. The plates were incubated at 37° C. for 3 hours then transferred to 28° C. for overnight incubation. The mating mixture was then lifted off the plate using sterile 9 cm Whatman glass microfibre filters and was transferred to a fresh LB plate containing ampicillin (100 ug/ml) and neomycin (100 ug/ml). After 2–3 days, individual ampR NeoR transconjugants were picked into wells of 96-well microliter dishes containing 100 ul minimal Pseudomonas media (LMG)+neomycin (100 ug/ml). The microliter plates were incubated overnight at 28° C. in an orbital shaker set at 200 rpm. After overnight incubation, 50 ul of 50% glycerol was added to each well, and the microtiter dishes were then maintained at −80° C. 10,000 individual mutants were collected and stored.

EXAMPLE 5

Screening Mutants for in vitro Fungai Inhibition Activity

Individual insertion mutants were spotted on to Neurospora culture agar (Difco) plates (150 mm) in ordered arrays. Re suspended mycelia fragments of *Neurospora crassa* were applied to the plates using a chromatography sprayer. After incubation overnight at 28° C., fungal mycelial growth formed an opaque background on the plate except in the immediate areas of the Pseudomonas colonies, where zones of clearing were observed. Pseudomonas mutants which produced zones of clearing which were either larger or visibly different than those of the wild-type parent were selected. Parent zones of clearing had a central clear core and outer concentric zone which formed a near linear gradient from clear on the inside to indistinguishable from the mycelial background on the outside.

EXAMPLE 6

Cultivation of Rhizoctonia solani for Greenhouse Biocontrol Assays

*Rhizoctonia solani* was grown on Potato Dextrose Agar (PDA, Difco), pH 5.6 in a petri dish. A 300 ml Erlenmeyer flask with 25 g mallet and 50 ml distilled water was autoclaved and incubated with one agar plug (5 mm diameter) from a PDA culture of *Rhizoctonia solani*. After incubation at 20° C. in the dark for 3 weeks the overgrown millet was airdried and ground in a Culatti mill (1 mm sieve, 6000 rpm).

EXAMPLE 7

Biocontrol Efficacy of Insertion Mutants

Insertion mutants which produced antifungal zones visibly different than the wildtype were tested in greenhouse biocontrol assays on cotton with the pathogen *Rhizoctonia solani*. Results for two mutants are shown in Table 1. Pseudomonas cultures were grown overnight in Luria broth at 28° C. For Trial 1, cells were pelleted by centrifugation, then resuspended in sterile water to an optical density of 2.5 at 600 nm (approximately $2 \times 10^9$ colony forming units per ml). For Trial 2, however, cells were diluted to an OD of 0.25 to enable greater differentiation in the biocontrol effects of the wild-type and mutant strains. *Rhizoctonia solani* was cultured on autoclaved millet, then dried and ground into powder. Soil was prepared by mixing equal pans of potting soil (Metro-mix 360), sand and vermiculite. This is used to fill 15 cm diameter pots. A 2 cm deep circular furrow with a total length of 30 cm was formed at the perimeter of each pot. Ten cotton seeds (Stoneville 506) were placed in each furrow. *R. solani*-infested millet powder was sprinkled evenly over the seeds in the furrows at the rate of 100 mg/pot, followed by the application of 20 ml of bacterial suspension for each pot. Water was added in place of bacterial suspension in the control. Each treatment consisted of four replicate pots for a total of 40 seeds per treatment. The plants were grown in an environmentally controlled chamber with a day/night temperature regime of 26/21° C. The plants were rated for disease severity after 10 days. Two mutants, CGA 319115 and CGA 321730, were shown to provide better disease control than the wild type parent CGA 267356. Table 1 shows results for these tests.

TABLE 1

Biocontrol Efficacy of CGA 319115 and CGA 321730

|  | Trial 1 | Trial 2 |
| --- | --- | --- |
| Rate of Application | $1.3 \times 10^9$ cfu/cm | $1.3 \times 10^8$ cfu/cm |
| No Pathogen Check | 100 | 100 |
| Pathogen Check | 0 | 0 |
| CGA 267356 | 46 | 0 |
| CGA 319115 | 69 | 60 |
| CGA 321730 | 73 | 90 |

Numbers reflecting the lack of disease symptoms on plants were assigned for individual plants on the scale of 1–5. Following summation within each treatment, the "no pathogen check" summation was normalized to 100, and the "pathogen check" summation was normalized to zero, with the three other treatment values being assigned accordingly.

While the present invention has been described with reference to specific embodiments thereof, it will be appreciated that numerous variations, modifications, and embodiments are possible, and accordingly, all such variations, modifications and embodiments are to be regarded as being within the scope of the present invention.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Deposits

The following Pseudomonas strains were deposited with the NRRL on Jan. 21, 1994, and were assigned the following Accession Numbers:

CGA 319115 NRRL B-21172

CGA 321730 NRRL B-21173

What is claimed is:

1. A biocontrol strain of Pseudomonas fluorescens designated CGA 319115 and deposited as NRRL B-21172.

2. A biocontrol strain of Pseudomonas fluorescens designated CGA 321730 and deposited as NRRL B-21173.

3. A method for controlling or inhibiting the growth of *Rhizoctania solani* fungus by applying an effective amount of biocontrol strain CGA 319115 deposited as NRRL B-21172 or CGA 321730 deposited as B-21173 to an environment in which the *Rhizoctania solani* fungus may grow.

4. A method for controlling or inhibiting the growth of *Rhizoctania solani* fungus by applying an effective amount of biocontrol strain CGA 319115 deposited as NRRL B-21172 or CGA 321730 deposited as B-21173 to a plant or plant part in order to protect said plant or plant part from *Rhizoctania solani* fungus.

5. A method for controlling or inhibiting the growth of *Rhizoctania solani* fungus by applying an effective amount of biocontrol strain CGA 319115 deposited as NRRL B-21172 or CGA 321730 deposited as B-21173 to seed in order to protect a plant which develops from said seed from *Rhizoctania solani* fungus.

* * * * *

SEQUENCE LISTING ( 1 ) GENERAL INFORMATION:

( i i i ) NUMBER OF SEQUENCES: 4

( 2 ) INFORMATION FOR SEQ ID NO:1:

( i ) SEQUENCE CHARACTERISTICS:
        ( A ) LENGTH: 12 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: Synthetic oligonucleotide used to
            ligate SalI ends in construction of pCIB113.

( x i ) SEQUENCE DESCRIPTION: SEQ ID NO:1:

TCGAGATCTA AA                                                                          1 2

( 2 ) INFORMATION FOR SEQ ID NO:2:

( i ) SEQUENCE CHARACTERISTICS:
        ( A ) LENGTH: 8 base pairs
        ( B ) TYPE: nucleic acid
        ( C ) STRANDEDNESS: single
        ( D ) TOPOLOGY: linear ( i i ) MOLECULE TYPE: other nucleic acid ( i x ) FEATURE:
        ( A ) NAME/KEY: misc_feature
        ( B ) LOCATION: 1..8
        ( D ) OTHER INFORMATION: /note="SYNTHETIC OLIGONUCLEOTIDE
            COMPLEMENTING RESIDUES 1 TO 8 OF SEQ. ID NO:1"

( x i ) SEQUENCE DESCRIPTION: SEQ ID NO:2:

TTTAGATC                                                                                       8

( 2 ) INFORMATION FOR SEQ ID NO:3:

( i ) SEQUENCE CHARACTERISTICS:
        ( A ) LENGTH: 36 base pairs
        ( B ) TYPE: nucleic acid (C) STRANDEDNESS: single
(D) TOPOLOGY: linear (ii) MOLECULE TYPE: other nucleic acid
  (A) DESCRIPTION: Synthetic oligonucleotide providing
      restriction sites, E.coli ribosome binding site and ATG
      translation start used for construction of pCIB114.

(xi) SEQUENCE DESCRIPTION: SEQ ID NO:3:

AAAGGAGATC TGGATCCAGG AGAAGCTTGC ATGCTA    36

(2) INFORMATION FOR SEQ ID NO:4:

(i) SEQUENCE CHARACTERISTICS:
    (A) LENGTH: 40 base pairs
    (B) TYPE: nucleic acid
    (C) STRANDEDNESS: single
    (D) TOPOLOGY: linear (ii) MOLECULE TYPE: other nucleic acid (ix) FEATURE:
    (A) NAME/KEY: misc_feature
    (B) LOCATION: 5..40
    (D) OTHER INFORMATION: /note="SYNTHETIC OLIGONUCLEOTIDE
        COMPLEMENTARY TO RESIDUES 1 TO 36 OF SEQ ID NO:3"

(xi) SEQUENCE DESCRIPTION: SEQ ID NO:4:

GATCTAGCAT GCAAGCTTCT CCTGGATCCA GATCTCCTTT    40